United States Patent
Moffarah et al.

(10) Patent No.: US 10,485,571 B2
(45) Date of Patent: Nov. 26, 2019

(54) BALLOON CATHETER WITH NON-DEPLOYABLE STENT HAVING IMPROVED STABILITY

(71) Applicant: AngioScore, Inc., Colorado Springs, CO (US)

(72) Inventors: Meir Moffarah, La Jolla, CA (US); Jeffrey Bleam, Boulder Creek, CA (US); Peter E. Wagner, Danville, CA (US)

(73) Assignee: ANGIOSCORE, INC., Colorado Springs, CO (US)

( * ) Notice: Subject to any disclaimer, the term of this patent is extended or adjusted under 35 U.S.C. 154(b) by 54 days.

(21) Appl. No.: 15/373,933

(22) Filed: Dec. 9, 2016

(65) Prior Publication Data
US 2017/0086877 A1 Mar. 30, 2017

Related U.S. Application Data

(63) Continuation of application No. 14/048,955, filed on Oct. 8, 2013, now Pat. No. 10,117,668.

(51) Int. Cl.
*A61B 17/3207* (2006.01)
*A61M 25/10* (2013.01)
*A61B 17/22* (2006.01)

(52) U.S. Cl.
CPC ... *A61B 17/320725* (2013.01); *A61M 25/104* (2013.01); *A61B 2017/22061* (2013.01); *A61M 2025/105* (2013.01); *A61M 2025/109* (2013.01)

(58) Field of Classification Search
CPC ............ A61M 25/104; A61M 25/1031; A61M 25/1086; A61M 25/109;
(Continued)

(56) References Cited

U.S. PATENT DOCUMENTS 2,701,559 A   2/1955  Cooper
2,854,983 A  10/1958  Baskin
(Continued)

FOREIGN PATENT DOCUMENTS

EP   0565796 B1   5/1997
EP   0623315 B1   6/1999
(Continued)

OTHER PUBLICATIONS

*AngioScore, Inc. v. Trireme Medical LLC et al*, Fourth Amended Complaint for: 1) Patent Infringement; 2) Breach of Fiduciary Duty Under California Law; 3) Breach of Fiduciary Duty Under Delaware Law; 4) Aiding and Abetting a Breach of Fiduciary Duty; and 5) Unfair Competition Under California Business and Professional Cos ss 17200, filed in the United States District Court, Northern District of California, Oakland Division, on Jul. 15, 2015, Case No. 4:12-cv-3393-YGR.
(Continued)

*Primary Examiner* — Martin T Ton

(57) ABSTRACT

An angioplasty catheter comprises a catheter body having a balloon or other radially expandable shell at its distal end. An external structure is carried over the shell and scores a stenosed region in a blood vessel when the balloon is inflated therein. The catheter has an attachment structure disposed between the catheter body and the balloon to accommodate foreshortening and rotation of the external structure as the balloon is expanded. The external structure may be part of a helical cage structure which floats over the balloon. Stabilizing struts are provided between at least some of the helical struts.

11 Claims, 6 Drawing Sheets

(58) Field of Classification Search
CPC .. A61M 2025/1031; A61M 2025/1084; A61B
17/3207; A61B 17/320725; A61B
2017/22061; A61B 2017/320733; A61B
2017/320008; A61B 2017/320741
USPC .............................. 606/159, 170; 604/103.09
See application file for complete search history.

(56) References Cited

U.S. PATENT DOCUMENTS

| | | |
|---|---|---|
| 3,045,677 A | 7/1962 | Wallace |
| 3,467,101 A | 9/1969 | Fogarty et al. |
| 3,825,013 A | 7/1974 | Craven |
| 4,327,736 A | 5/1982 | Inoue |
| 4,456,011 A | 6/1984 | Warnecke |
| 4,483,340 A | 11/1984 | Fogarty et al. |
| 4,604,762 A | 8/1986 | Robinson |
| 4,637,396 A | 1/1987 | Cook |
| 4,649,922 A | 3/1987 | Wiktor |
| 4,723,549 A | 2/1988 | Wholey et al. |
| 4,733,665 A | 3/1988 | Palmaz |
| 4,796,629 A | 1/1989 | Grayzel |
| 4,838,853 A | 6/1989 | Parisi |
| 4,887,613 A | 12/1989 | Farr et al. |
| 4,895,166 A | 1/1990 | Farr et al. |
| 4,921,484 A | 5/1990 | Hillstead |
| 4,942,788 A | 7/1990 | Farr et al. |
| 4,950,277 A | 8/1990 | Farr |
| 4,956,830 A | 9/1990 | Mock et al. |
| 4,969,458 A | 11/1990 | Wiktor |
| 4,976,711 A | 12/1990 | Parins et al. |
| 4,986,807 A | 1/1991 | Farr |
| 4,986,830 A | 1/1991 | Owens et al. |
| 4,998,539 A | 3/1991 | Delsanti |
| 5,003,918 A | 4/1991 | Olson et al. |
| 5,019,088 A | 5/1991 | Farr |
| 5,019,089 A | 5/1991 | Farr |
| 5,026,384 A | 6/1991 | Farr et al. |
| 5,062,384 A | 11/1991 | Foley et al. |
| 5,062,648 A | 11/1991 | Gomringer |
| 5,071,407 A | 12/1991 | Termin et al. |
| 5,098,440 A | 3/1992 | Hillstead |
| 5,100,386 A | 3/1992 | Inoue |
| 5,100,423 A | 3/1992 | Fearnot |
| 5,101,682 A | 4/1992 | Radisch et al. |
| 5,102,402 A | 4/1992 | Dror et al. |
| 5,102,417 A | 4/1992 | Palmaz |
| 5,108,416 A | 4/1992 | Ryan et al. |
| 5,112,345 A | 5/1992 | Farr |
| 5,116,318 A | 5/1992 | Hillstead |
| 5,120,322 A | 6/1992 | Davis et al. |
| 5,133,732 A | 7/1992 | Wiktor |
| 5,176,693 A | 1/1993 | Pannek et al. |
| 5,181,911 A | 1/1993 | Shturman |
| 5,190,058 A | 3/1993 | Jones et al. |
| 5,192,291 A | 3/1993 | Pannek et al. |
| 5,196,024 A | 3/1993 | Barath |
| 5,209,727 A | 5/1993 | Radisch et al. |
| 5,222,971 A | 6/1993 | Willard et al. |
| 5,224,945 A | 7/1993 | Pannek et al. |
| 5,224,949 A | 7/1993 | Gomringer et al. |
| 5,226,887 A | 7/1993 | Farr et al. |
| 5,243,997 A | 9/1993 | Uflacker et al. |
| 5,263,963 A | 11/1993 | Garrison et al. |
| 5,295,493 A | 3/1994 | Radisch et al. |
| 5,295,959 A | 3/1994 | Gurbel et al. |
| 5,304,121 A | 4/1994 | Sahatjian |
| 5,306,250 A | 4/1994 | March et al. |
| 5,308,354 A | 5/1994 | Zacca et al. |
| 5,308,356 A | 5/1994 | Blackshear, Jr. et al. |
| 5,318,576 A | 6/1994 | Plassche et al. |
| 5,320,634 A | 6/1994 | Vigil et al. |
| 5,336,178 A | 8/1994 | Kaplan et al. |
| 5,336,234 A | 8/1994 | Vigil et al. |
| 5,344,401 A | 9/1994 | Radisch et al. |
| 5,344,419 A | 9/1994 | Spears |
| 5,350,101 A | 9/1994 | Godlewski |
| 5,423,745 A | 6/1995 | Todd et al. |
| 5,443,078 A | 8/1995 | Uflacker |
| 5,443,446 A | 8/1995 | Shturman |
| 5,443,496 A | 8/1995 | Schwartz et al. |
| 5,449,372 A | 9/1995 | Schmaltz et al. |
| 5,449,373 A | 9/1995 | Pinchasik et al. |
| 5,456,666 A | 10/1995 | Campbell et al. |
| 5,456,667 A | 10/1995 | Ham et al. |
| 5,458,568 A | 10/1995 | Racchini et al. |
| 5,460,607 A | 10/1995 | Miyata et al. |
| 5,470,314 A | 11/1995 | Walinsky |
| 5,501,694 A | 3/1996 | Ressemann et al. |
| 5,524,635 A | 6/1996 | Uflacker et al. |
| 5,527,282 A | 6/1996 | Segal |
| 5,536,178 A | 7/1996 | Novelli |
| 5,545,132 A | 8/1996 | Fagan et al. |
| 5,556,405 A | 9/1996 | Lary |
| 5,556,408 A | 9/1996 | Farhat |
| 5,562,620 A | 10/1996 | Klein et al. |
| 5,569,195 A | 10/1996 | Saab |
| 5,571,086 A | 11/1996 | Kaplan et al. |
| 5,607,442 A | 3/1997 | Fischell et al. |
| 5,609,574 A | 3/1997 | Kaplan et al. |
| 5,616,149 A | 4/1997 | Barath |
| 5,620,457 A | 4/1997 | Pinchasik et al. |
| 5,624,433 A | 4/1997 | Radisch et al. |
| 5,628,746 A | 5/1997 | Clayman |
| 5,628,755 A | 5/1997 | Heller et al. |
| 5,643,210 A | 7/1997 | Iacob |
| 5,649,941 A | 7/1997 | Lary |
| 5,681,281 A | 10/1997 | Vigil et al. |
| 5,690,642 A | 11/1997 | Osborne et al. |
| 5,695,469 A | 12/1997 | Segal |
| 5,697,944 A | 12/1997 | Lary |
| 5,697,971 A | 12/1997 | Fischell et al. |
| 5,702,410 A | 12/1997 | Klunder et al. |
| 5,707,385 A | 1/1998 | Williams |
| 5,713,863 A | 2/1998 | Vigil et al. |
| 5,713,913 A | 2/1998 | Lary et al. |
| 5,718,684 A | 2/1998 | Gupta |
| 5,730,698 A | 3/1998 | Fischell et al. |
| 5,733,303 A | 3/1998 | Israel et al. |
| 5,735,816 A | 4/1998 | Lieber et al. |
| 5,742,019 A | 4/1998 | Radisch et al. |
| 5,755,708 A | 5/1998 | Segal |
| 5,755,781 A | 5/1998 | Jayaraman |
| 5,766,201 A | 6/1998 | Ravenscroft et al. |
| 5,766,238 A | 6/1998 | Lau et al. |
| 5,772,681 A | 6/1998 | Leoni |
| 5,776,141 A | 7/1998 | Klein et al. |
| 5,776,181 A | 7/1998 | Lee et al. |
| 5,792,144 A | 8/1998 | Fischell et al. |
| 5,792,415 A | 8/1998 | Hijlkema |
| 5,797,935 A | 8/1998 | Barath |
| 5,807,355 A | 9/1998 | Ramzipoor et al. |
| 5,810,767 A | 9/1998 | Klein |
| 5,814,061 A | 9/1998 | Osborne et al. |
| 5,827,321 A | 10/1998 | Roubin et al. |
| 5,863,284 A | 1/1999 | Klein |
| 5,868,708 A | 2/1999 | Hart et al. |
| 5,868,719 A | 2/1999 | Tsukernik |
| 5,868,779 A | 2/1999 | Ruiz |
| 5,868,783 A | 2/1999 | Tower |
| 5,869,284 A | 2/1999 | Cao et al. |
| 5,891,090 A | 4/1999 | Thornton |
| 5,902,475 A | 5/1999 | Trozera et al. |
| 5,904,679 A | 5/1999 | Clayman |
| 5,904,698 A | 5/1999 | Thomas et al. |
| 5,906,639 A | 5/1999 | Rudnick et al. |
| 5,916,166 A | 6/1999 | Reiss et al. |
| 5,919,200 A | 7/1999 | Stambaugh et al. |
| 5,954,742 A | 9/1999 | Osypka |
| 5,961,490 A | 10/1999 | Adams |
| 5,967,984 A | 10/1999 | Chu et al. |
| 5,980,486 A | 11/1999 | Enger |
| 5,987,661 A | 11/1999 | Peterson |
| 5,994,667 A | 11/1999 | Merdan et al. |
| 6,013,055 A | 1/2000 | Bampos et al. |

(56) References Cited

U.S. PATENT DOCUMENTS

| | | |
|---|---|---|
| 6,036,686 A | 3/2000 | Griswold |
| 6,036,689 A | 3/2000 | Tu et al. |
| 6,036,708 A | 3/2000 | Sciver |
| 6,048,356 A | 4/2000 | Ravenscroft et al. |
| 6,053,913 A | 4/2000 | Tu et al. |
| 6,059,811 A | 5/2000 | Pinchasik et al. |
| 6,071,285 A | 6/2000 | Lashinski et al. |
| 6,071,286 A | 6/2000 | Mawad |
| 6,077,298 A | 6/2000 | Tu et al. |
| RE36,764 E | 7/2000 | Zacca et al. |
| 6,102,904 A | 8/2000 | Vigil et al. |
| 6,106,548 A | 8/2000 | Roubin et al. |
| 6,117,104 A | 9/2000 | Fitz |
| 6,117,153 A | 9/2000 | Lary et al. |
| 6,123,718 A | 9/2000 | Tu et al. |
| 6,129,706 A | 10/2000 | Janacek |
| 6,129,708 A | 10/2000 | Enger |
| 6,136,011 A | 10/2000 | Stambaugh |
| 6,146,323 A | 11/2000 | Fischell |
| 6,152,944 A | 11/2000 | Holman et al. |
| 6,156,254 A | 12/2000 | Andrews et al. |
| 6,156,265 A | 12/2000 | Sugimoto |
| 6,165,187 A | 12/2000 | Reger |
| 6,190,356 B1 | 2/2001 | Bersin |
| 6,190,403 B1 | 2/2001 | Fischell et al. |
| 6,193,686 B1 | 2/2001 | Estrada et al. |
| 6,203,569 B1 | 3/2001 | Wijay |
| 6,206,910 B1 | 3/2001 | Berry et al. |
| 6,210,392 B1 | 4/2001 | Vigil et al. |
| 6,224,625 B1 | 5/2001 | Jayaraman |
| 6,235,043 B1 | 5/2001 | Reiley et al. |
| 6,241,762 B1 | 6/2001 | Shanley |
| 6,245,040 B1 | 6/2001 | Inderbitzen et al. |
| 6,258,087 B1 | 7/2001 | Edwards et al. |
| 6,258,099 B1 | 7/2001 | Mareiro et al. |
| 6,258,108 B1 | 7/2001 | Lary |
| 6,261,319 B1 | 7/2001 | Kveen et al. |
| 6,261,630 B1 | 7/2001 | Nazarova et al. |
| 6,287,336 B1 | 9/2001 | Globerman et al. |
| 6,289,568 B1 | 9/2001 | Miller et al. |
| 6,296,651 B1 | 10/2001 | Lary et al. |
| 6,306,151 B1 | 10/2001 | Lary |
| 6,306,166 B1 | 10/2001 | Barry et al. |
| 6,309,414 B1 | 10/2001 | Rolando et al. |
| 6,312,459 B1 | 11/2001 | Huang et al. |
| 6,319,229 B1 | 11/2001 | Kim et al. |
| 6,319,242 B1 | 11/2001 | Patterson et al. |
| 6,319,251 B1 | 11/2001 | Tu et al. |
| 6,325,779 B1 | 12/2001 | Zedler |
| 6,325,813 B1 | 12/2001 | Hektner |
| 6,332,880 B1 | 12/2001 | Yang et al. |
| 6,355,013 B1 | 3/2002 | van Muiden |
| 6,355,059 B1 | 3/2002 | Richter et al. |
| 6,361,545 B1 | 3/2002 | Macoviak et al. |
| 6,364,856 B1 | 4/2002 | Ding et al. |
| 6,371,961 B1 | 4/2002 | Osborne et al. |
| 6,394,995 B1 | 5/2002 | Solar et al. |
| 6,416,494 B1 | 7/2002 | Wilkins |
| 6,416,539 B1 | 7/2002 | Hassdenteufel |
| 6,425,882 B1 | 7/2002 | Vigil |
| 6,425,908 B2 | 7/2002 | Ravenscroft et al. |
| 6,440,158 B1 | 8/2002 | Saab |
| 6,447,501 B1 | 9/2002 | Solar et al. |
| 6,450,988 B1 | 9/2002 | Bradshaw |
| 6,450,989 B2 | 9/2002 | Dubrul et al. |
| 6,454,775 B1 | 9/2002 | Demarais et al. |
| 6,471,979 B2 | 10/2002 | New et al. |
| 6,475,233 B2 | 11/2002 | Trozera |
| 6,475,234 B2 | 11/2002 | Richter et al. |
| 6,475,236 B1 | 11/2002 | Roubin et al. |
| 6,478,807 B1 | 11/2002 | Foreman et al. |
| 6,500,186 B2 | 12/2002 | Lafontaine et al. |
| 6,517,765 B1 | 2/2003 | Kelley |
| 6,540,722 B2 | 4/2003 | Boyle et al. |
| 6,551,310 B1 | 4/2003 | Ganz et al. |
| 6,554,795 B2 | 4/2003 | Bagaoisan et al. |
| 6,562,062 B2 | 5/2003 | Jenusaitis et al. |
| 6,565,528 B1 | 5/2003 | Mueller |
| 6,569,180 B1 | 5/2003 | Sirhan et al. |
| 6,575,993 B1 | 6/2003 | Yock |
| 6,592,548 B2 | 7/2003 | Jayaraman |
| 6,602,281 B1 | 8/2003 | Klein |
| 6,605,107 B1 | 8/2003 | Klein |
| 6,607,442 B2 | 8/2003 | Ogata et al. |
| 6,613,072 B2 | 9/2003 | Lau et al. |
| 6,616,678 B2 | 9/2003 | Nishtala et al. |
| 6,626,861 B1 | 9/2003 | Hart et al. |
| 6,632,231 B2 | 10/2003 | Radisch et al. |
| 6,648,912 B2 | 11/2003 | Trout et al. |
| 6,652,548 B2 | 11/2003 | Evans et al. |
| 6,656,351 B2 | 12/2003 | Boyle |
| 6,663,660 B2 | 12/2003 | Dusbabek et al. |
| 6,695,813 B1 | 2/2004 | Boyle et al. |
| 6,743,196 B2 | 6/2004 | Barbut et al. |
| 6,746,463 B1 | 6/2004 | Schwartz |
| 6,783,542 B2 | 8/2004 | Eidenschink |
| 6,840,950 B2 | 1/2005 | Stanford et al. |
| 6,872,206 B2 | 3/2005 | Edwards et al. |
| 6,918,920 B1 | 7/2005 | Wang et al. |
| 6,939,320 B2 | 9/2005 | Lennox |
| 6,942,680 B2 | 9/2005 | Grayzel et al. |
| 6,951,566 B2 | 10/2005 | Lary |
| 7,004,968 B2 * | 2/2006 | Lootz .................... A61F 2/91 623/1.15 |
| 7,011,654 B2 | 3/2006 | Dubrul et al. |
| 7,011,670 B2 | 3/2006 | Radisch et al. |
| 7,029,483 B2 | 4/2006 | Schwartz |
| 7,060,051 B2 | 6/2006 | Palasis |
| 7,131,981 B2 | 11/2006 | Appling et al. |
| 7,172,609 B2 | 2/2007 | Radisch et al. |
| 7,186,237 B2 | 3/2007 | Meyer et al. |
| 7,232,432 B2 | 6/2007 | Fulton et al. |
| 7,252,650 B1 | 8/2007 | Andrews et al. |
| 7,303,572 B2 | 12/2007 | Melsheimer et al. |
| 7,354,445 B2 | 4/2008 | Nicholson et al. |
| 7,357,813 B2 | 4/2008 | Burgermeister |
| 7,396,358 B2 | 7/2008 | Appling et al. |
| 7,455,652 B2 | 11/2008 | Laird |
| 7,465,311 B2 | 12/2008 | Wang et al. |
| 7,494,497 B2 | 2/2009 | Weber |
| 7,517,352 B2 | 4/2009 | Evans et al. |
| 7,524,319 B2 | 4/2009 | Dubrul |
| 7,566,319 B2 | 7/2009 | McAuley et al. |
| 7,686,824 B2 | 3/2010 | Konstantino et al. |
| 7,691,119 B2 | 4/2010 | Farnan |
| 7,708,748 B2 | 5/2010 | Weisenburgh, II et al. |
| 7,708,753 B2 | 5/2010 | Hardert |
| 7,736,375 B2 | 6/2010 | Crow |
| 7,763,043 B2 | 7/2010 | Goodin et al. |
| 7,780,715 B2 | 8/2010 | Shaked et al. |
| 7,780,798 B2 | 8/2010 | Stinson et al. |
| 7,931,663 B2 | 4/2011 | Farnan et al. |
| 7,955,350 B2 | 6/2011 | Konstantino et al. |
| 7,963,942 B2 | 6/2011 | Chen |
| 7,976,557 B2 | 7/2011 | Kunis |
| 7,998,184 B2 | 8/2011 | Eidenschink |
| 8,043,259 B2 | 10/2011 | Radisch et al. |
| 8,052,703 B2 | 11/2011 | St. Martin et al. |
| 8,066,726 B2 | 11/2011 | Kelley |
| 8,080,026 B2 | 12/2011 | Konstantino et al. |
| 8,123,770 B2 | 2/2012 | Olsen et al. |
| 8,192,675 B2 | 6/2012 | Burton et al. |
| 8,221,444 B2 | 7/2012 | Wang et al. |
| 8,323,307 B2 | 12/2012 | Hardert |
| 8,348,987 B2 | 1/2013 | Eaton |
| 8,382,820 B2 | 2/2013 | Addonizio et al. |
| 8,454,637 B2 | 6/2013 | Aggerholm et al. |
| 8,574,248 B2 | 11/2013 | Kassab |
| 8,685,050 B2 | 4/2014 | Schur et al. |
| 8,685,990 B2 | 4/2014 | Coats et al. |
| 2001/0001113 A1 | 5/2001 | Lim et al. |
| 2001/0001823 A1 | 5/2001 | Ryan |
| 2001/0007082 A1 | 7/2001 | Dusbabek et al. |
| 2001/0012950 A1 | 8/2001 | Nishtala et al. |

(56) References Cited

U.S. PATENT DOCUMENTS

| | | |
|---|---|---|
| 2001/0016753 A1 | 8/2001 | Caprio et al. |
| 2001/0031981 A1 | 10/2001 | Evans et al. |
| 2002/0010487 A1 | 1/2002 | Evans et al. |
| 2002/0010489 A1 | 1/2002 | Grayzel et al. |
| 2002/0029015 A1 | 3/2002 | Camenzind et al. |
| 2002/0038144 A1 | 3/2002 | Trout et al. |
| 2002/0045930 A1 | 4/2002 | Burg et al. |
| 2002/0065548 A1 | 5/2002 | Birdsall et al. |
| 2002/0077606 A1 | 6/2002 | Trotta |
| 2002/0111633 A1 | 8/2002 | Stoltze et al. |
| 2002/0165599 A1 | 11/2002 | Nasralla |
| 2002/0193873 A1 | 12/2002 | Brucker et al. |
| 2003/0018376 A1 | 1/2003 | Solar et al. |
| 2003/0023200 A1 | 1/2003 | Barbut et al. |
| 2003/0028235 A1 | 2/2003 | McIntosh et al. |
| 2003/0032973 A1 | 2/2003 | Jenusaitis et al. |
| 2003/0065381 A1 | 4/2003 | Solar et al. |
| 2003/0074046 A1 | 4/2003 | Richter |
| 2003/0078606 A1 | 4/2003 | Lafontaine et al. |
| 2003/0097169 A1 | 5/2003 | Brucker et al. |
| 2003/0105509 A1 | 6/2003 | Jang et al. |
| 2003/0114915 A1 | 6/2003 | Mareiro et al. |
| 2003/0144683 A1 | 7/2003 | Sirhan et al. |
| 2003/0149468 A1 | 8/2003 | Wallsten |
| 2003/0152870 A1 | 8/2003 | Huang |
| 2003/0153870 A1 | 8/2003 | Meyer et al. |
| 2003/0171799 A1 | 9/2003 | Lee et al. |
| 2003/0187494 A1 | 10/2003 | Loaldi |
| 2003/0195609 A1 | 10/2003 | Berenstein et al. |
| 2003/0199970 A1 | 10/2003 | Shanley |
| 2003/0199988 A1 | 10/2003 | Devonec et al. |
| 2003/0208244 A1 | 11/2003 | Stein et al. |
| 2003/0208255 A1 | 11/2003 | O'Shaughnessy et al. |
| 2004/0034384 A1 | 2/2004 | Fukaya |
| 2004/0111108 A1 | 6/2004 | Farnan |
| 2004/0127475 A1 | 7/2004 | New et al. |
| 2004/0133223 A1 | 7/2004 | Weber |
| 2004/0143287 A1 | 7/2004 | Konstantino et al. |
| 2004/0210299 A1 | 10/2004 | Rogers et al. |
| 2004/0230293 A1 | 11/2004 | Yip et al. |
| 2004/0243158 A1 | 12/2004 | Konstantino et al. |
| 2005/0010278 A1 | 1/2005 | Vardi et al. |
| 2005/0021070 A1 | 1/2005 | Feld et al. |
| 2005/0021071 A1* | 1/2005 | Konstantino .. A61B 17/320725 606/194 |
| 2005/0049677 A1 | 3/2005 | Farnan |
| 2005/0083768 A1 | 4/2005 | Hara |
| 2005/0131512 A1 | 6/2005 | Vonderwalde |
| 2005/0137690 A1 | 6/2005 | Salahieh et al. |
| 2005/0271844 A1 | 12/2005 | Mapes et al. |
| 2006/0015133 A1 | 1/2006 | Grayzel et al. |
| 2006/0074484 A1 | 4/2006 | Huber |
| 2006/0085025 A1 | 4/2006 | Farnan et al. |
| 2006/0112536 A1 | 6/2006 | Herweck et al. |
| 2006/0129093 A1 | 6/2006 | Jackson |
| 2006/0149308 A1 | 7/2006 | Melsheimer et al. |
| 2006/0173487 A1 | 8/2006 | Uflacker et al. |
| 2006/0184191 A1 | 8/2006 | O'Brien |
| 2006/0247674 A1 | 11/2006 | Roman |
| 2006/0259005 A1 | 11/2006 | Konstantino et al. |
| 2006/0259062 A1 | 11/2006 | Konstantino |
| 2006/0270193 A1 | 11/2006 | Hidaka et al. |
| 2007/0112422 A1 | 5/2007 | Dehdashtian |
| 2007/0185513 A1 | 8/2007 | Woolfson et al. |
| 2007/0198047 A1 | 8/2007 | Schon et al. |
| 2007/0213808 A1 | 9/2007 | Roubin et al. |
| 2008/0300610 A1 | 12/2008 | Chambers |
| 2009/0105686 A1 | 4/2009 | Snow et al. |
| 2009/0105687 A1 | 4/2009 | Deckman et al. |
| 2009/0264859 A1 | 10/2009 | Mas |
| 2009/0281490 A1 | 11/2009 | McAuley et al. |
| 2009/0306582 A1 | 12/2009 | Granada et al. |
| 2010/0042121 A1 | 2/2010 | Schneider et al. |
| 2010/0121372 A1* | 5/2010 | Farnan ............... A61F 2/86 606/194 |
| 2010/0179647 A1 | 7/2010 | Carpenter et al. |
| 2010/0286720 A1 | 11/2010 | Shaked et al. |
| 2010/0286721 A1 | 11/2010 | Goodin et al. |
| 2011/0082483 A1 | 4/2011 | Diamant et al. |
| 2011/0125247 A1 | 5/2011 | Farnan et al. |
| 2011/0152905 A1* | 6/2011 | Eaton ............... A61B 17/22 606/159 |
| 2011/0160756 A1 | 6/2011 | Aggerholm et al. |
| 2011/0264039 A1 | 10/2011 | Thielen et al. |
| 2011/0270177 A1 | 11/2011 | Chambers et al. |
| 2012/0059401 A1 | 3/2012 | Konstantino et al. |
| 2012/0065660 A1 | 3/2012 | Ferrera et al. |
| 2012/0215251 A1 | 8/2012 | Burton et al. |
| 2012/0232638 A1 | 9/2012 | Diamant et al. |
| 2012/0245607 A1* | 9/2012 | Gershony ...... A61B 17/320725 606/159 |
| 2012/0277626 A1 | 11/2012 | Burbank et al. |
| 2013/0041391 A1 | 2/2013 | Spencer et al. |
| 2013/0041399 A1 | 2/2013 | Hardert |
| 2013/0060127 A1 | 3/2013 | Burton et al. |
| 2013/0066346 A1 | 3/2013 | Pigott |
| 2013/0096604 A1 | 4/2013 | Hanson et al. |
| 2013/0150874 A1 | 6/2013 | Kassab |
| 2013/0211381 A1 | 8/2013 | Feld |
| 2013/0218181 A1 | 8/2013 | Feld et al. |
| 2013/0226220 A1 | 8/2013 | Konstantino et al. |
| 2013/0253554 A1 | 9/2013 | Gershony et al. |
| 2013/0345730 A1 | 12/2013 | Gershony et al. |
| 2014/0058358 A1 | 2/2014 | Kassab |
| 2014/0066960 A1 | 3/2014 | Feld et al. |
| 2014/0142598 A1 | 5/2014 | Fulton et al. |
| 2015/0100079 A1 | 4/2015 | Moffarah et al. |
| 2016/0331400 A1 | 11/2016 | Gershony et al. |

FOREIGN PATENT DOCUMENTS

| | | |
|---|---|---|
| EP | 1169970 A1 | 1/2002 |
| EP | 1179323 A2 | 2/2002 |
| EP | 0832608 B1 | 3/2003 |
| EP | 1042997 B1 | 3/2005 |
| EP | 1581298 B1 | 8/2006 |
| EP | 1414373 B1 | 5/2008 |
| EP | 1337198 B1 | 6/2009 |
| EP | 1748816 B1 | 7/2010 |
| EP | 2063924 B1 | 10/2010 |
| EP | 2283890 A1 | 2/2011 |
| EP | 1962696 B1 | 3/2012 |
| EP | 1737530 B1 | 3/2013 |
| EP | 2564890 A1 | 3/2013 |
| JP | H06505416 A | 6/1994 |
| JP | 2002126086 A | 5/2002 |
| JP | 2002126086 A1 | 5/2002 |
| JP | 2004504111 A | 2/2004 |
| JP | 2004148013 A1 | 5/2004 |
| JP | 2007502694 A | 2/2007 |
| JP | 2007530158 A | 11/2007 |
| JP | 2011528963 A | 12/2011 |
| JP | 2011529350 A | 12/2011 |
| WO | WO1991002494 A1 | 3/1991 |
| WO | 9217118 A1 | 10/1992 |
| WO | WO1993001753 A2 | 2/1993 |
| WO | WO1994010919 A1 | 5/1994 |
| WO | WO1994023787 A1 | 10/1994 |
| WO | WO1994024946 A1 | 11/1994 |
| WO | WO1995003083 A1 | 2/1995 |
| WO | WO1998005377 A1 | 2/1998 |
| WO | WO1998045506 A1 | 10/1998 |
| WO | 1999017680 A1 | 4/1999 |
| WO | 1999055253 A1 | 11/1999 |
| WO | 1999062430 A1 | 12/1999 |
| WO | 02083011 A1 | 10/2002 |
| WO | WO2002083011 A1 | 10/2002 |
| WO | WO2003026536 A1 | 4/2003 |
| WO | WO2003039628 A2 | 5/2003 |
| WO | WO2003041760 A2 | 5/2003 |
| WO | WO2004028610 A2 | 4/2004 |
| WO | WO2004060460 A2 | 7/2004 |
| WO | WO2004066852 A2 | 8/2004 |
| WO | WO2005025458 A1 | 3/2005 |

(56) References Cited

FOREIGN PATENT DOCUMENTS

| WO | 2009150099 A1 | 12/2009 |
|---|---|---|
| WO | 2012040225 A2 | 3/2012 |
| WO | 2015054277 A1 | 4/2015 |

OTHER PUBLICATIONS

*AngioScore, Inc.* v. *Trireme Medical, LLC*, Defendant's Exhibit DX4222, United States District Court, Northern District of California, Oakland Division, Case No. 4:12-cv-3393-YGR (U.S. Pat. No. 5,797,935 to Barath).
*AngioScore, Inc.* v. *Trireme Medical, LLC*, Defendant's Exhibit DX4224, United States District Court, Northern District of California, Oakland Division, Case No. 4:12-cv-3393-YGR (U.S. Pat. No. 5,868,783 to Tower).
*AngioScore, Inc.* v. *Trireme Medical, LLC*, Defendant's Exhibit DX4268, United States District Court, Northern District of California, Oakland Division, Case No. 4:12-cv-3393-YGR (U.S. Pat. No. 5,730,698 to Fischel) et al.).
*AngioScore, Inc.* v. *Trireme Medical, LLC*, Defendant's Exhibit DX4272, United States District Court, Northern District of California, Oakland Division, Case No. 4:12-cv-3393-YGR (U.S. Pat. No. 6,059,811 to Pinchasik et al.).
*AngioScore, Inc.* v. *Trireme Medical, LLC*, Defendant's Exhibit DX4273, United States District Court, Northern District of California, Oakland Division, Case No. 4:12-cv-3393-YGR (U.S. Pat. No. 6,261,319 to Kveen et al.).
*AngioScore, Inc.* v. *Trireme Medical, LLC*, Defendant's Exhibit DX4274, United States District Court, Northern District of California, Oakland Division, Case No. 4:12-cv-3393-YGR (U.S. Pat. No. 6,416,539 to Hassdenteufel).
*AngioScore, Inc.* v. *Trireme Medical, LLC*, Defendant's Exhibit DX4315, United States District Court, Northern District of California, Oakland Division, Case No. 4:12-cv-3393-YGR (Zarge, et al., Chapter 17: Balloon Angioplasty, in Peripheral Endovascular Insterventions (1996)).
*AngioScore, Inc.* v. *Trireme Medical, LLC*, Defendant's Exhibit DX4473, United States District Court, Northern District of California, Oakland Division, Case No. 4:12-cv-3393-YGR (U.S. Pat. No. 5,196,024 to Barath).
*AngioScore, Inc.* v. *Trireme Medical, LLC*, Judgement as Modified by the Court, filed Oct. 14, 2015, United States District Court, Northern District of California, Oakland Division, Case No. 4:12-cv-3393-YGR.
*AngioScore, Inc.* v. *Trireme Medical, LLC*, Order Construing Claims in Dispute; Granting in Part and Denying in Part Defendants' Motion for Summary Judgment of Non-Infrignment, filed Jun. 25, 2014, United States District Court, Northern District of California, Oakland Division, Case No. 4:12-cv-3393-YGR.
*AngioScore, Inc.* v. *Trireme Medical, LLC*, Reporter's Transcript of Proceedings, Sep. 21, 2015, vol. 12, United States District Court, Northern District of California, Oakland Division, Case No. 4:12-cv-3393-YGR (including testimony by Robert Farnan).
*AngioScore, Inc.* v. *Trireme Medical, LLC*, Reporter's Transcript of Proceedings, Sep. 22, 2015, vol. 13, United States District Court, Northern District of California, Oakland Division, Case No. 4:12-cv-3393-YGR (including testimony by Ali Almedhychy).
*AngioScore, Inc.* v. *Trireme Medical, LLC*, Reporter's Transcript of Proceedings, vol. 14, Sep. 28, 2015, United States District Court, Northern District of California, Oakland Division, Case No. 4:12-cv-3393-YGR (including testimony by Michael Horzewski, jury instructions including meaning of claim terms, and closing arguments).
*AngioScore, Inc.* v. *Trireme Medical, LLC*, United States District Court, Northern District of California, Oakland Division, Case No. 4:12-cv-3393-YGR, Defendant's Exhibit DX4362 (Palmaz, et al., "Atherosclerotic Rabbit Aortas: Expandable Intraluminal Grafting," Radiology, Sep. 1986, pp. 724-726).
*AngioScore, Inc.* v. *Trireme Medical, LLC*, Verdict Form filed Sep. 29, 2015, United States District Court, Northern District of California, Oakland Division, Case No. 4:12-cv-3393-YGR.
European search report and search opinion dated May 4, 2010 for EP 06770116.9.
European search report and search opinion dated Dec. 28, 2009 for EP 05792875.6.
Exhibit A to *AngioScore, Inc.* v. *Trireme Medical, LLC*, Fourth Amended Complaint filed Jul. 15, 2014, United States District Court, Northern District of California, Oakland Division, Case No. 4:12-cv-3393-YGR.
Extended European Search Report issued in EP Application 14852692. 4, dated May 4, 2017, 12 pages.
Extended European Search Report issued in EP Application No. 11827369.7, dated Apr. 7, 2014. 6 pages.
File History for U.S. Appl. No. 12/694,163, filed Jan. 26, 2010 entitled Balloon Catheter With Non-Deployable Stent.
File History for U.S. Appl. No. 13/022,489, filed Feb. 7, 2011 entitled Balloon Catheter With Non-Deployable Stent.
File History for U.S. Appl. No. 13/489,250, filed Jun. 5, 2012, entitled Balloon Catheter With Non-Deployable Stent.
File History for U.S. Appl. No. 13/044,425, filed Mar. 9, 2011 (not attached).
First Examination Report dated Feb. 5, 2014 from corresponding EP Application No. 05733012.8.
International Preliminary Report on Patentability issued in PCT/US2014/059525, dated Apr. 21, 2016, 5 pages.
International search report and written opinion dated Feb. 27, 2007 for PCT/US2006/017872.
International search report and written opinion dated May 23, 2006 for PCT /2005/009571.
International search report and written opinion dated Jul. 26, 2007 for PCT/2005/028809.
International search report and written opinion dated Nov. 4, 2004 for PCT/2004/000177.
International Search Report and Written Opinion issued in PCT/US2011/052392 dated Jan. 11, 2012, 7 pages.
International Search Report issued in PCT/US2002/035547dated May 20, 2003 , 3 Pages.
International Search Report issued in PCT/US2004/027836 dated Dec. 30, 2004 , 1 Page.
Japanese office action dated Jul. 9, 2010 for JP 2007-505113. (in Japanese with English translation).
Supplementary European Search Report dated Nov. 20, 2013 from corresponding EP Application No. 05733012.8.

* cited by examiner

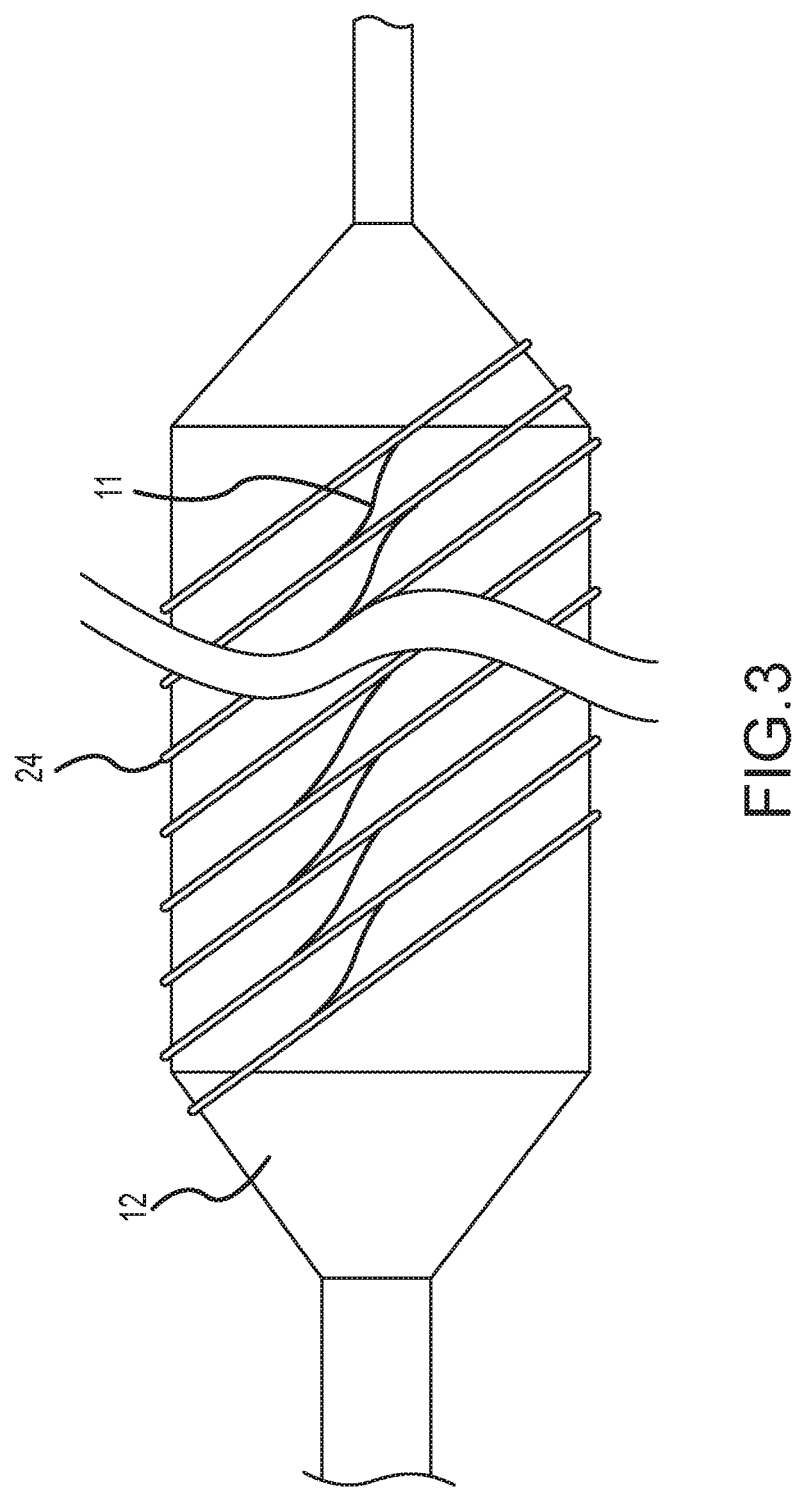

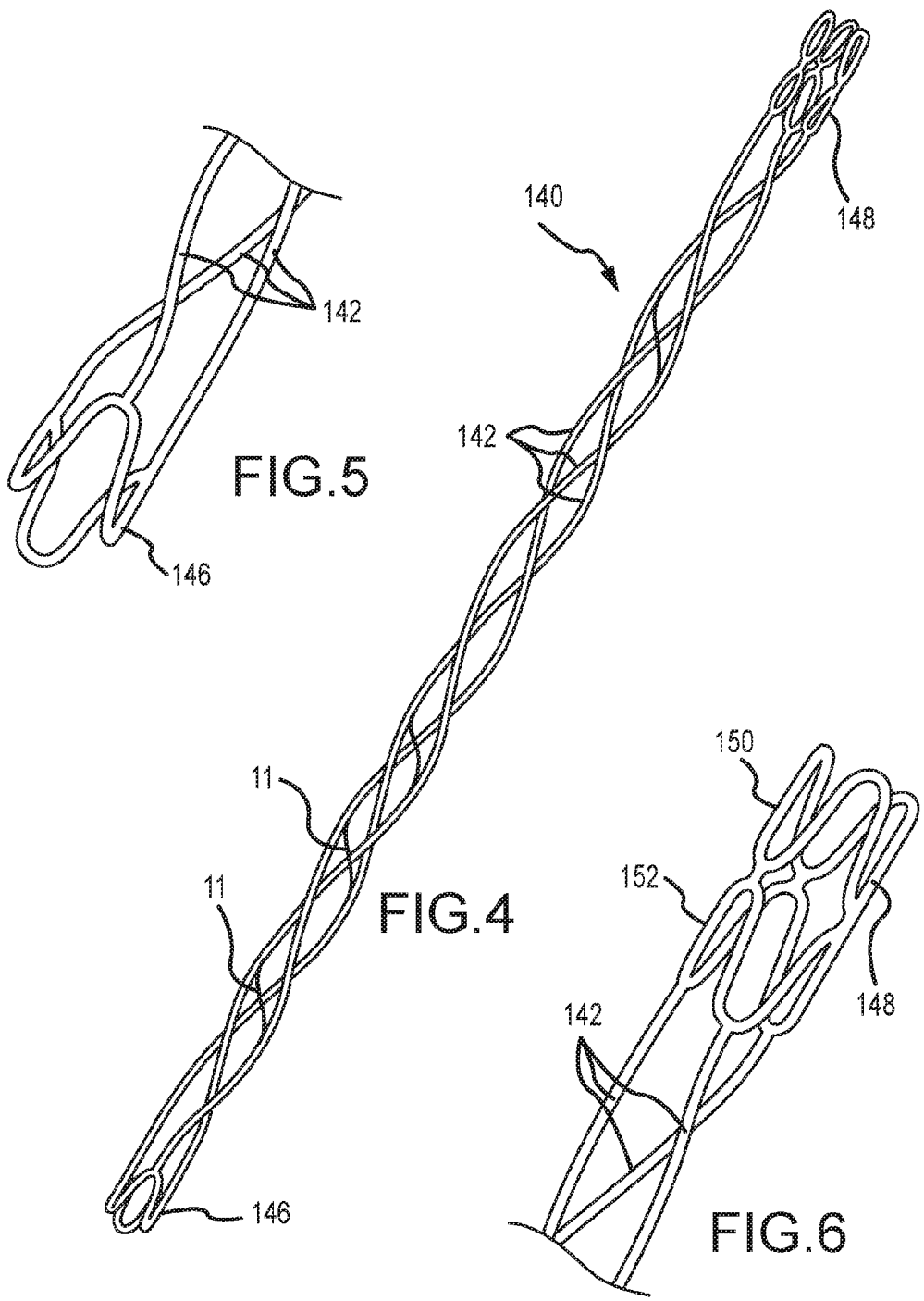

BALLOON CATHETER WITH NON-DEPLOYABLE STENT HAVING IMPROVED STABILITY

CROSS-REFERENCE TO RELATED APPLICATION

The present application is a continuation of U.S. patent application Ser. No. 14/048,955, filed Oct. 8, 2013, entitled "BALLOON CATHETER WITH NON-DEPLOYABLE STENT HAVING IMPROVED STABILITY," the entirety of each of which is herein incorporated by reference for all purposes.

RELATED APPLICATIONS

This application relates to U.S. patent application Ser. No. 13/841,755, filed Mar. 15, 2013, which is a continuation of U.S. patent application Ser. No. 13/292,716, filed on Nov. 9, 2011 (now U.S. Pat. No. 8,454,636), which is a continuation of U.S. patent application Ser. No. 10/917,917, filed on Aug. 13, 2004, now U.S. Pat. No. 8,080,026, which is a continuation-in-part of application Ser. No. 10/810,330, filed on Mar. 25, 2004, now U.S. Pat. No. 7,955,350, which is a continuation-in-part of application Ser. No. 10/631,499, filed on Jul. 30, 2003, now U.S. Pat. No. 7,686,824.

BACKGROUND OF THE INVENTION

Field of the Invention

The present invention relates to the field of medical devices, more specifically to medical devices intended to treat stenoses in the vascular system.

Balloon dilatation (angioplasty) is a common medical procedure mainly directed at revascularization of stenotic vessels by inserting a catheter having a dilatation balloon through the vascular system. The balloon is inflated inside a stenosed region in a blood vessel in order to apply radial pressure to the inner wall of the vessel and widen the stenosed region to enable better blood flow.

In many cases, the balloon dilatation procedure is immediately followed by a stenting procedure where a stent is placed to maintain vessel patency following the angioplasty. Failure of the angioplasty balloon to properly widen the stenotic vessel, however, may result in improper positioning of the stent in the blood vessel. If a drug-eluting stent is used, its effectiveness may be impaired by such improper positioning and the resulting restenosis rate may be higher. This is a result of several factors, including the presence of gaps between the stent and the vessel wall, calcified areas that were not treated properly by the balloon, and others.

Conventional balloon angioplasty suffers from a number of other shortcomings as well. In some cases the balloon dilatation procedure causes damage to the blood vessel due to aggressive balloon inflation that may stretch the diseased vessel beyond its elastic limits. Such over inflation may damage the vessel wall and lead to restenosis of the section that was stretched by the balloon. In other cases, slippage of the balloon during the dilatation procedure may occur. This may result in injury to the vessel wall surrounding the treated lesion. One procedure in which slippage is likely to happen is during treatment of in-stent restenosis, which at present is difficult to treat by angioplasty balloons. Fibrotic lesions are also hard to treat with conventional balloons, and elastic recoil is usually observed after treatment of these lesions. Many long lesions have fibrotic sections that are difficult to treat using angioplasty balloons.

An additional problem associated with balloon angioplasty treatment has been the "watermelon seed effect." Angioplasty is carried out at very high pressures, typically up to twenty atmospheres or higher, and the radially outward pressure of the balloon can cause axial displacement of the balloon in a manner similar to squeezing a watermelon seed with the fingers. Such axial displacement, of course, reduces the effectiveness of balloon dilatation. Another problem with conventional angioplasty balloon design has been deflation of the balloon. Even after the inflation medium is removed from a balloon, the deflated configuration will have a width greater than the original folded configuration which was introduced to the vasculature. Such an increase in profile can make removal of the balloon difficult.

Atherectomy/Thrombectomy devices intended to remove plaque/thrombus material may also include a structure that expands in a lesion while the plaque/thrombus removal mechanism is within this structure. The removed material is either being stacked in the catheter or sucked out thru the catheter. When the procedure is done, the expandable structure is collapsed and the catheter removed. Foreign object removal devices usually include a basket structure that needs to be expanded to collect the object and then collapse for retrieval. Distal protection devices usually include a basket structure that support a mesh that needs to be expanded distal to the treated lesion to collect the loose objects and then collapse for retrieval.

These devices usually include an elastic metallic material that needs to be expanded in the vascular system to fulfill its task and afterwards collapse to a small diameter to facilitate retrieval. The transition between the collapsed (closed) configuration to the expanded (open) configuration can be done in two ways: the structure can be at a normally closed (collapsed) configuration in which force is applied to cause the structure to expand. In this case, the elastic recoil of the structure will cause it to collapse back to closed configuration when the expanding force ceases. The structure may also be at a normally open (expanded) configuration in which a constraining element is forced over it to hold it down for the collapsed configuration (for example a constraining tube). When this constraining element is removed the structure is free to expand to the expanded (open) configuration. The structure material may also be non-elastic. In this case, the structure will need to be forced to transit between both collapsed and expanded configurations.

One problem associated with conventional angioplasty expansion systems is that the transition between the collapsed and expanded configurations involves significant rotational and axial reaction forces. These reaction forces are applied by the structure on the catheter as a result of the force applied by the catheter to expand or close the structure. Axial reaction forces are created due the foreshortening of the structure during expansion. Rotational reaction forces (torques) are created when a non-longitudinal element is forced to expand/collapse. Since the catheters are usually less stiff than the structure, these reaction forces may cause the structure to not expand or collapse properly, or cause undesired deformation to the catheter itself.

For these reasons, it would be desirable to provide improved cutting or scoring balloon designs and methods for their use. In particular, it would be desirable to provide cutting or scoring balloons which are highly flexible over the length of the balloon structure, which readily permit deflation and facilitate removal from the vasculature, and which are effective in treating all forms of vascular stenoses, including but not limited to treatment of highly calcified plaque regions of diseased arteries, treatment of small vessels and/or vessel bifurcations that will not be stented, treatment of ostial lesions, and treatment of in-stent restenosis (ISR). Moreover, it would be desirable if such balloon structures and methods for their use could provide for improved anchoring of the balloon during dilatation of the stenosed region.

It would further be desirable to minimize the reaction forces applied by the external structure to the catheter, and at the same time be able to control the expansion of the expandable structure. It would also be desirable to adjust the compliance and improve the shape stability of the system in a predictable way without changing the materials or geometry of the expandable structure. At least some of these objectives will be met with the inventions described hereinafter.

BRIEF SUMMARY OF THE INVENTION

The present invention provides improved apparatus and methods for the dilatation of stenosed regions in the vasculature. The stenosed regions will often include areas of fibrotic, calcified, or otherwise hardened plaque or other stenotic material of the type which can be difficult to dilatate using conventional angioplasty balloons. The methods and apparatus will often find their greatest use in treatment of the arterial vasculature, including but not limited to the coronary arterial vasculature, but may also find use in treatment of the venous and/or peripheral vasculature, treatment of small vessels and/or vessel bifurcations that will not be stented, treatment of ostial lesions, and treatment of ISR.

In a first aspect of the present invention a method of dilating a stenosed region in a blood vessel is disclosed. The method includes introducing a helical scoring structure having a distal end and a proximal end carried over a balloon, wherein the helical scoring structure comprises a plurality of helical elements that longitudinally extend from the distal end to the proximal end, and a plurality of stabilizing struts spaced along the length of the helical scoring structure and coupled to at least two adjacent helical elements, expanding the balloon to dilate the helical scoring structure within the stenosed region within the blood vessel, wherein the proximal end of the helical scoring structure, which is free to move axially, moves distally and the scoring structure shortens to accommodate such distal movement of the helical scoring structure as the balloon is expanded; holding the expanded helical scoring structure in place to disrupt the stenoses; and deflating the balloon causing the helical structure to collapse. The stabilizing struts enhance the ability of the scoring structure to maintain its desired shape.

The helical scoring structure means that the structure will be able to score or cut stenotic material within a treated blood vessel along lines which are generally in a non-axial direction. For example, the scoring lines may be helical, serpentine, zig-zag, or may combine some axial components together with such non-axial components. Usually, the non-axial scoring pattern which is imparted will include scoring segments which, when taken in total, circumscribe at least a majority of and usually the entire inside wall of the blood vessel up to one time, preferably more than one time, usually more than two times, often at least three times, more often at least four, five, six, or more times. It is believed that the resulting scoring patterns which circumscribe the inner wall of the vessel will provide improved results during subsequent balloon dilatation.

Usually the scoring structure will comprise at least one continuous, i.e., non-broken, scoring element having a length of at least 0.5 cm, more usually at least 1 cm, often at least 2 cm, usually at least 3 cm, and sometimes at least 4 cm or more. Alternatively, the scoring structure may comprise a plurality of much smaller segments which may be arranged in a helical or other pattern over the balloon, typically having a length in the range from 0.1 cm to 2 cm, often being 0.5 cm or less, sometimes being 0.3 cm or less. Additionally, the scoring structure elements may be adjoined to one another with one or more stabilizing struts. Rather than to extend along the entire length of the scoring structure, the stabilizing struts are configured to couple one scoring element with an adjacent scoring element.

In order to promote scoring of the blood vessel wall when the underlying expandable shell is expanded, the scoring structure will usually have a vessel contact area which is 20% or less of the area of the expandable shell, usually being below 10%, and often being in the range from 1% to 5% of the area of the expandable shell. The use of a shell having such a relatively small contact area increases the amount of force applied to the vascular wall through the structure by expansion of the underlying expandable shell. The scoring structure can have a variety of particular configurations, often being in the form of a wire or slotted tube having a circular, square, or other cross-sectional geometry. Preferably, the components of the scoring structure will comprise a scoring edge, either in the form of a honed blade, a square shoulder, or the like. A presently preferred scoring edge is electropolished and relatively small.

In a preferred embodiment, the scoring structure may be formed as a separate expandable cage which is positioned over the expandable shell of the catheter. The cage will usually have a collar or other attachment structure at each end for placement on the catheter body on either side of the expandable shell. A collar may be a simple tube, and other attachment structures will usually be crimpable or otherwise mechanically attachable to the catheter body, such as a serpentine or other ring structure. The attachment structures on the cage may be attached at both ends to the catheter body, but will more usually be attached at only a single end with the other end being allowed to float freely. Such freedom allows the scoring structure to shorten as the structure is expanded on the expandable shell. In certain embodiments, both ends of the scoring structure will be fixed to the catheter body, but at least one of the attachment structures will have a spring or other compliant attachment component which provides an axial extension as the center of the scoring structure foreshortens.

In many cases, since the scoring elements are non-axial, there are torques induced during the expansion of the balloon and the shortening of the scoring structure. These torques may be high, and if one end of the scoring structure is constrained from rotation, the scoring element will not expand properly. The final expanded configuration of the scoring element is achieved via shortening and rotation.

In a preferred embodiment, both sides of the scoring element are fixed to the catheter, but at least one side will have a compliant structure which will provide axial tension and at the same time will allow the scoring element to rotate to its final configuration.

In some cases both ends of the scoring element are fixed and the shortening is achieved by deformation of the wire. For example, the wire can have a secondary structure which permits elongation (e.g., it may be a coiled filament) or can be formed from a material which permits elongation, e.g., nitinol. The scoring element can be attached in both ends, in a way that will allow rotation. In the case were the torques are low (depending on the design of the scoring element) there is no need for rotation and the torque can be absorbed either by the scoring element or by the catheter.

In all cases, the scoring structure is preferably composed of an elastic material, more preferably a super elastic material, such as nitinol. The scoring structure is thus elastically expanded over the expandable shell, typically an inflatable balloon similar to a conventional angioplasty balloon. Upon deflation, the scoring structure will elastically close to its original non-expanded configuration, thus helping to close and contain the balloon or other expandable shell.

In some cases the scoring element will be a combination of more than one material. In one case the scoring element can be made from nitinol and parts of it can be made from stainless steel. In other cases the scoring element can be made of stainless steel or nitinol and part of it can be made from polymer to allow high deformations.

In other preferred embodiments, the assembly of the shell and the scoring structure will be sufficiently flexible to permit passage through tortuous regions of the vasculature, e.g., being capable of bending at radius of 10 mm or below when advanced through 45°, 90°, or higher bends in the coronary vasculature. Usually, the scoring structure will comprise one or more scoring elements, wherein less than 70% of the cumulative length of the scoring element is aligned axially on the shell when expanded, preferably being less than 50% of the cumulative length, and more preferably being less than 25% of the cumulative length. In other instances, the scoring structure may comprise one or more scoring elements, wherein the cumulative length of the scoring element includes a non-axial component of at least 10 mm, preferably at least 12 mm, and more preferably 36 mm. Preferably, at least some of the scoring elements will have scoring edges which are oriented radially outwardly along at least a major portion of their lengths at all times during inflation and deflation and while inflated. By "radially outward," it is meant that an edge or shoulder of the element will be oriented to score the stenotic material or the interior wall of the treated vessel, particularly as the shell is being inflated.

The scoring elements will usually, but not necessarily, have a scoring edge formed over at least a portion of their lengths. A "scoring edge" may comprise a rounded or square such as found on a wire. The scoring elements will concentrate the radially outward force of the balloon to cause scoring or other disruption of the plaque or other stenotic material being treated.

In a second aspect of the present invention, the scoring catheter comprises a catheter body and a radially expandable shell, generally as set forth above. The scoring catheter includes a helical scoring structure having a distal end and a proximal end carried over a balloon, wherein the helical scoring structure is configured to radially expand in response to balloon inflation and further comprises a plurality of helical elements that longitudinally extend from the distal end to the proximal end, and a plurality of stabilizing struts spaced along the length of the helical scoring structure and coupled to at least two adjacent helical elements, and a catheter body configured to carry the helical scoring structure at a distal end.

In a third aspect of the present invention, an expansible scoring cage adapted to be carried over a balloon of a balloon catheter is disclosed. The expansible scoring cage includes an assembly having a plurality of helical scoring elements, wherein said assembly is normally in a radially collapsed configuration and expansible over a balloon to a radially expanded configuration, wherein the assembly returns to its radially collapsed configuration when the balloon is deflated; further wherein the plurality of helical scoring elements are coupled to each other via a plurality of stabilizing struts along the longitudinal length of the helical scoring elements.

An elongated scoring structure is carried over the shell, and the assembly of the shell and the scoring structure will be highly flexible to facilitate introduction over a guide wire, preferably being sufficiently flexible when unexpanded so that it can be bent at an angle of at least 90°, preferably 180°, at a radius of 1 cm without kinking or otherwise being damaged. Such flexibility can be determined, for example, by providing a solid cylinder having a radius of 1 cm and conforming the assembly of the scoring structure and expandable shell over the cylinder. Alternatively, the assembly can be advanced over a guide wire or similar element having a 180° one centimeter radius bend. In either case, if the assembly bends without kinking or other damage, it meets the requirement described above. Other specific features in this further embodiment of the catheters of the present invention are as described above in connection with the prior embodiments.

In still another aspect of the apparatus of the present invention, an expandable scoring cage is adapted to be carried over a balloon of a balloon catheter. The scoring cage comprises an assembly of one or more elongate elastic scoring elements arranged in a non-axial pattern. As defined above, the non-axial pattern may comprise both axial and non-axial segments. The assembly is normally in a radially collapsed configuration and is expandable over a balloon to a radially expanded configuration. After the balloon is deflated, the assembly returns to a radially collapsed configuration, preferably being assisted by the elastic nature of the scoring cage and a series of stabilizing struts. Advantageously, the scoring cage with stabilizing struts will enhance uniform expansion of the underlying balloon or other expandable shell and will inhibit "dog boning" where an angioplasty balloon tends to over inflate at each end, increasing the risk of vessel dissection. The scoring elements will be adapted to score hardened stenotic material, such as plaque or fibrotic material, when expanded by the balloon in a blood vessel lumen. The scoring cage may be adapted to mount over the balloon with either or both ends affixed to the balloon, generally as described above in connection with prior embodiments. Preferred geometries for the scoring elements include those which circumscribe the balloon, those which are arranged helically over the balloon, those which are arranged in a serpentine pattern over balloon and the like.

In yet another aspect of the present invention, a method for dilatating a stenosed region in a blood vessel comprises radially expanding a shell which carries a scoring structure. The scoring structure scores and dilates the stenosed region and includes one or more non-axial scoring elements arranged to impart a circumscribing score pattern about the inner wall of the blood vessel as the shell is expanded. The stenosed region is typically characterized by the presence of calcified plaque, fibrotic plaque, or other hardened stenotic material which is preferably scored prior to dilatation. Preferably, the scoring structure will not be moved in an axial direction while engaged against the stenosed region, and the scoring structure may optionally be free from axially scoring elements.

In still another aspect of the present invention, an angioplasty catheter comprises a catheter body and a radially expandable shell near the distal end of the catheter body. An external structure, such as a scoring structure or cutting structure, is carried over but unattached to the shell. The catheter further comprises an attachment structure having a proximal end and a distal end attached to the scoring structure, wherein the attachment structure is sufficiently sized and compliant to accommodate reaction forces or geometrical changes produced by the scoring structure as it is expanded by the shell. Generally, at least a portion of said scoring structure is arranged helically over the shell. However, the scoring structure may comprise numerous different configurations as described above.

In one aspect of the present invention, the proximal end of the attachment structure is fixed to the catheter body and the distal end of the attachment structure is secured to the proximal end of the scoring structure. In all cases, the attachment structure is capable of axially and rotationally extending to accommodate foreshortening of the scoring structure as the shell is expanded.

It is understood that other embodiments of the specific teachings herein will become readily apparent to those skilled in the art from the following detailed description, wherein it is shown and described only several embodiments of the teachings by way of illustration. As will be realized, the subject matter of the teachings herein is capable of other and different embodiments and its several details are capable of modification in various other respects, all without departing from the spirit and scope of these teachings. Accordingly, the drawings and detailed description are to be regarded as illustrative in nature and not as restrictive.

BRIEF DESCRIPTION OF THE DRAWINGS

FIGS. 3, 3A, and 3B illustrate self-closing cage configurations in accordance with the embodiments of the invention.

FIG. 4 illustrates an alternative embodiment of a helical scoring structure comprising serpentine and zigzag structures for mounting onto a balloon catheter.

FIG. 5 illustrates a first of the serpentine mounting elements of the scoring structure of FIG. 4.

FIG. 6 illustrates a second of the serpentine mounting elements of the scoring structure of FIG. 4.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Embodiments of the present invention relate to a device for revascularization of stenotic vessels and specifically to a balloon catheter having external scoring elements. The dilatation device comprises a conventional dilatation balloon such as a polymeric balloon and a helical scoring structure. Alternatively, other scoring configurations may be mounted on the balloon catheter without departing from the teachings disclosed herein.

Figure 1:
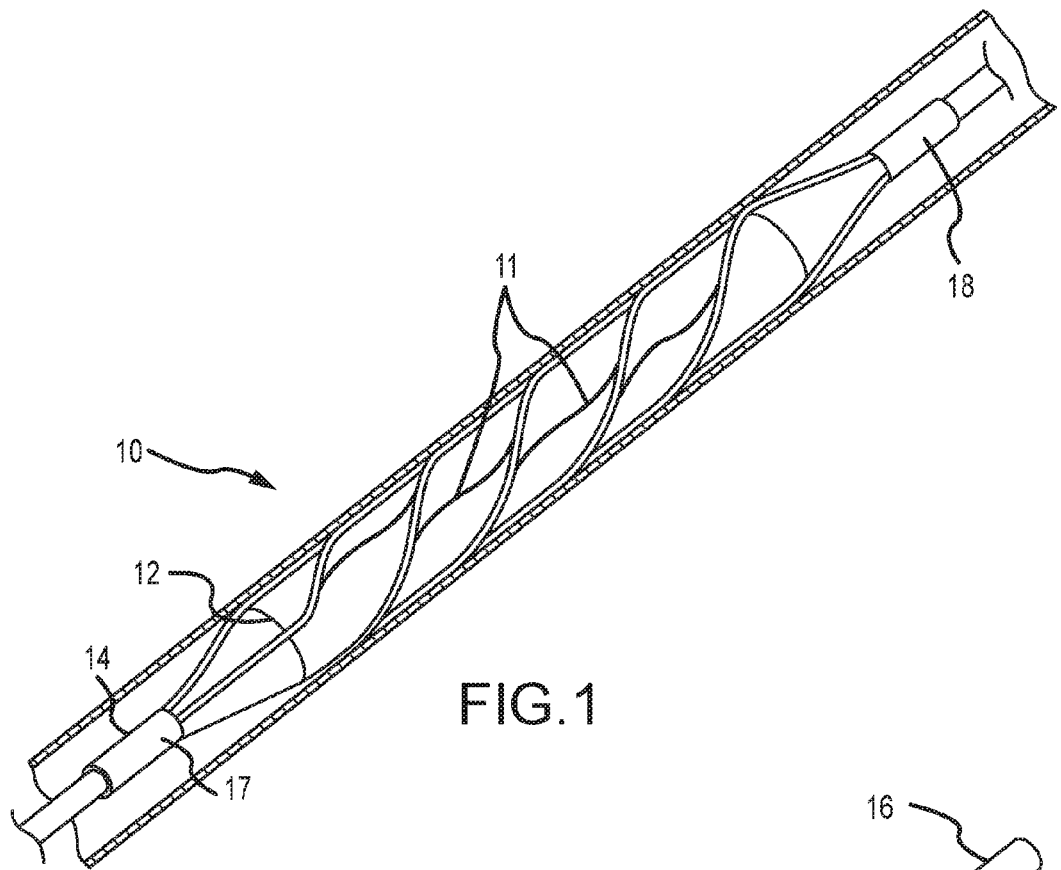
FIGS. 1, 1A, 1B, and 1C are schematic illustrations of the balloon scoring structure embodiment in accordance with an embodiment of the invention.
Figure 1A:
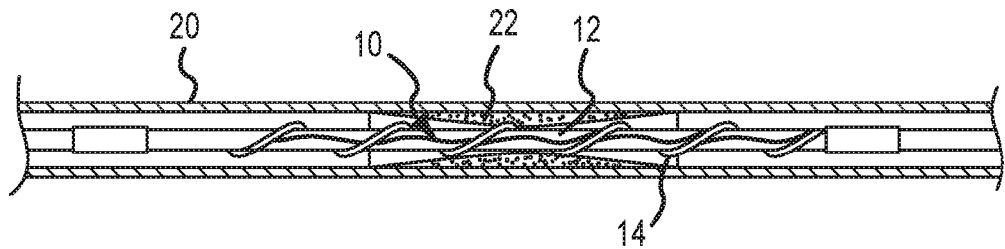
Figure 1B:
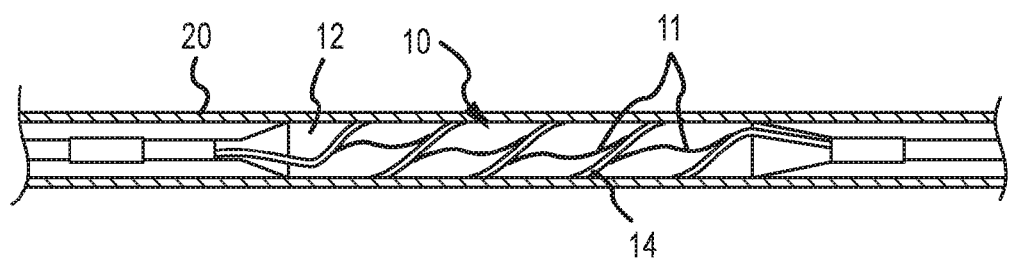

Reference is now made to FIGS. 1, 1A, and 1B, which are schematic illustrations of a dilatation device 10 in accordance with embodiments described herein. The dilatation device 10 includes a dilatation balloon 12, which may be any conventional angioplasty balloon such as commonly used by interventional cardiologists or radiologists, and a helical assembly 14 mounted over or attached to the dilatation balloon 12. The helical assembly 14 also includes at least one stabilizing strut 11 that couples one longitudinal strut to an adjacent longitudinal strut, as depicted in FIG. 1. Preferably, the helical assembly 14 will incorporate a series of stabilizing struts that extend about the longitudinal length of the helical assembly 14. For added stability, the stabilizing struts 11 may be spaced evenly or unevenly along the longitudinal axis of the helical assembly 14. Helical unit 14 may be attached at 17 and 18 to the catheter shaft proximate to proximal and distal ends of the balloon 12 by collar-like attachments 15 and 16 (See FIG. 2).

The stabilizing struts 11 may additionally provide for the long scoring elements of the helical assembly 14 to deploy in an evenly spaced manner during balloon inflation to various pressures. The stabilizing struts 11 may also minimize the possibility that the scoring element struts or wires will bunch together during device operation, and, still further, assist with keeping the scoring elements from lifting from the balloon surface at its deflated state, thereby facilitating device pull back. In other words, as will be appreciated by one of ordinary skill, the incorporation of stabilizing struts 11 may create a stable support structure between the otherwise independently floating struts (See FIG. 2). The stabilizing strut(s) 11 may have at least one bend along its path extending from one scoring element to an adjacent scoring element—or the same scoring element in the single wire embodiment. The at least one bend, preferably at least two, would facilitate maintaining the narrow profile of the collapsed helical structure for unobstructed removal of the catheter from the body lumen post-treatment. Moreover, the points at which the stabilizing strut 11 meets the two adjacent helical elements may be typically offset along the longitudinal axis to accommodate the expanded and collapsed configurations without having any helical scoring elements or stabilizing struts detach or otherwise stray from the scoring structure's profile.

Further, the compliance of the balloon and the scoring element(s) should be chosen to assure uniform expansion of the balloon substantially free from "dog-boning" as the combined structure expands within a lesion. If a compliant or a semi-compliant balloon is used and the compliance of the scoring element was not matched to comply with the properties of the balloon, the expansion of the balloon-scoring element system will not be uniform. This non-uniformity may impair the efficacy of the scoring catheter and, in some cases, may result in poor performance. For example, under given pressure, certain parts of the balloon 12 will be able to expand while other parts will be constrained by excessive resistance of the scoring elements.

The helical unit or assembly 14 is typically made of nitinol. Helical unit 14 may be made of other metals such as stainless steel, cobalt-chromium alloy, titanium, and the like. Alternatively, helical unit 14 may be a polymeric helix, or made of another elastic material. Helical unit 14 may be attached at its proximal and distal ends to the catheter shaft proximate to the proximal end 17 and distal end 18 of dilatation balloon 12. Alternatively, helical unit 14 may be attached to the catheter shaft proximate to the distal end and/or the proximal end of dilatation balloon 12 by collar-like attachment elements 15 and 16. (See FIG. 2). Still further, one or both collar-like attachments 15 and 16 may be free to slide on the catheter shaft. Spring or other compliant elements may be alternatively or additionally provided as part of the attachment elements to accommodate shortening of the helical unit 14 as it is expanded.

Dilatation device 10 is inserted into the vascular system, for example, using a conventional catheter procedure, to a region of stenotic material 22 of blood vessel 20. (The term "stenotic" is used herein to refer to the vascular lesion, e.g., the narrowed portion of the vessel that the balloon is meant to open.) At the stenotic area 22, the dilatation balloon 12 is inflated, for example, by liquid flow into the balloon. Helical unit 14 widens on the inflated dilatation balloon 12. On inflation, the dilatation balloon 12 together with the helical unit 14 is pressed against the walls of blood vessel 20 as shown in FIG. 1B.

Figure 1C:
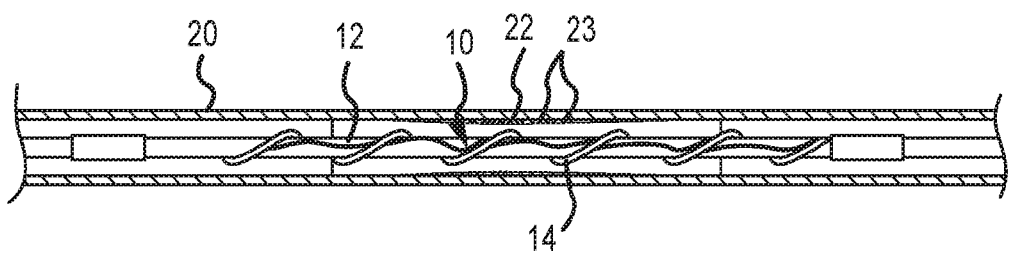

Reference is now made to FIG. 1C, illustrating blood vessel 20 after the deflation of dilatation balloon 12. Helical unit 14 narrows when deflating the dilatation balloon 12, thus the dilatation device 10 is narrowed and may be readily retrieved from blood vessel 20. The deflation profile of the balloon 10 is low and mainly circular. The stenotic material 22 in blood vessel 20 is pressed against blood vessel 20 walls to widen the available lumen and enhance blood flow. The pressing of helical unit 14 against the walls of blood vessel 20 causes scoring 23 in the stenotic area.

Helical unit 14 may be pushed outwardly by the inflation of the balloon 12, and is stretched by the inflation of the balloon. When the balloon is deflated, helical unit 14 assists in the deflation by its elastic recoil. This active deflation is faster and also leads to a low profile of the deflated balloon. The balloon 12 is disposed within the helical unit 14, which returns to its pre-inflated shape and forces the balloon to gain a low radial profile.

In another embodiment of the invention, dilatation device 10 may carry a stent. The stent can be crimped over the helical unit 14. In this way, the helical unit 14 can push the stent against hard areas of the lesion, enabling proper positioning of the stent against the vessel wall, even in hard-calcified lesions without pre-dilation.

Figure 2:
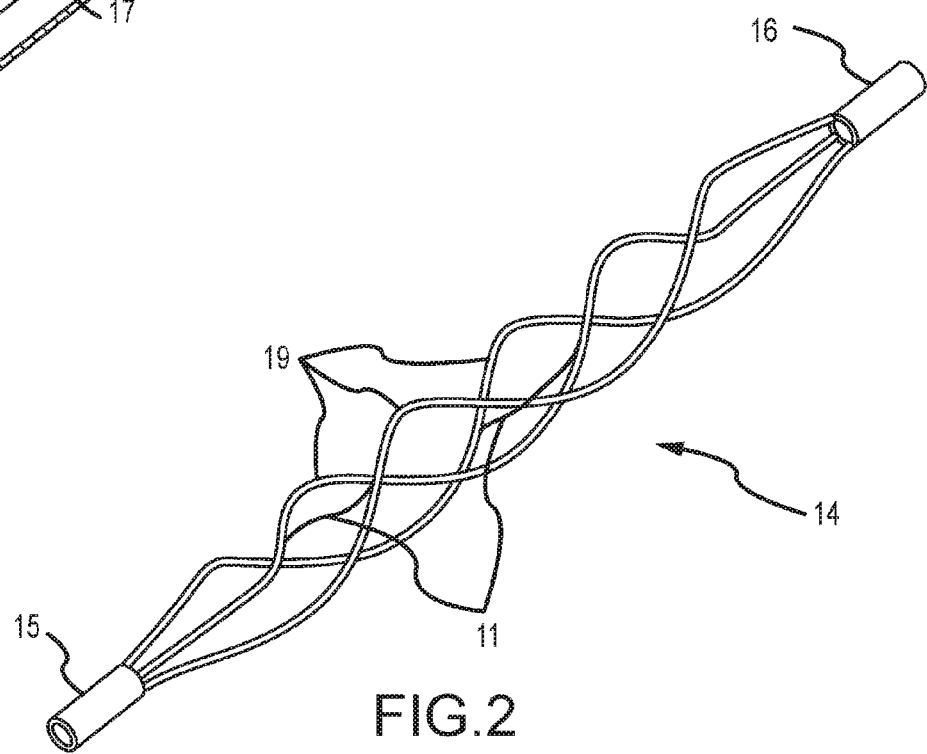
FIG. 2 is a schematic illustration of an exemplary helical scoring structure embodiment in accordance with embodiments of the invention.

Reference is now made to FIG. 2, illustrating the helical unit 14 in accordance with embodiments of the invention. Helical unit 14 is typically made of nitinol. Helical unit 14 includes but is not limited to three wires 19 that are attached to collars 15 and 16 at the proximal end and distal end, respectively. As depicted in connection with FIG. 2, stabilizing struts 11 are coupled between adjacent scoring elements, in this embodiment, wires 19. Alternatively, the scoring structure may comprise wires of other elements attached directly to the balloon material or close to the balloon ends.

Wires 19 are attached between collars 15 and 16. The diameter of the wires is typically in the range of 0.05 mm to 0.5 mm. Alternatively, a cage (for example a metallic cage made of a slotted tube) can be used in several configurations that allow local stress concentrations. The size and shape of the cross section of the cage elements or the cross section of the wires can vary. The cross section can be a circle, rectangle, triangle, or other shape.

In alternative embodiments, the wires 19 may comprise short segments that are attached to the balloon 12. In further alternative embodiments of the invention, the helical unit 14 may be glued, thermally bonded, fused, or mechanically attached at one or both ends to the dilatation balloon 12. In yet another embodiment, a scoring structure may comprise wires that are attached to the dilatation balloon 12 in a helical configuration or other configuration. The wires may be thermally attached to the balloon 12, glued, mechanically attached, or the like. In still another embodiment, a scoring structure comprises wire or cage elements that are not parallel to the longitudinal axis of the balloon 12 so that the combination of the scoring structure 19 and the balloon 12 remains flexible.

In additional embodiments, the combination of dilatation balloon 12 and scoring structure scores the lesion and provides better vessel preparation for drug eluting stents by allowing better positioning of the stent against the vessel wall and diffusion of the drug through the scores in the lesion. In these embodiments, the balloon can be used as a platform to carry drugs to the lesion where scoring of the lesion can enhance delivery of the drug to the vessel wall. The balloon may then be used for local drug delivery by embedding drug capsules, drug containing polymer, and the like, through the stenotic material and into the vessel wall.

The scoring structures may be attached directly to the balloons or other shells, in some cases being embedded in the balloon material, but will more usually be formed as separate cage structures which are positioned over the balloon and attached to the catheter through attachment elements on either side of the balloon. The expandable cages may be formed using conventional medical device fabrication techniques, such as those used for fabricating stents, such as laser cutting of hypotube and other tubular structures, EDM forming of hypotubes and tubes, welding of wires and other components and the like.

Typically, such expandable shell structures will comprise the attachment elements and an intermediate scoring section between the attachment elements. As illustrated in the embodiments above, the attachment elements may be simple cylindrical or tube structures which circumscribe the catheter body on either side of the balloon or other expandable shell. The simple tube structures may float over the catheter body, i.e., be unattached, or may be fixed to the catheter body. A number of alternative embodiments for the attachment elements will be described in connection with the embodiments below.

The intermediate scoring sections may also have a variety of configurations where at least some of the scoring elements will typically be disposed in a non-axial configuration, i.e., in a direction which is not parallel to the axial direction of the expandable cage. A preferred configuration for the intermediate scoring section comprises one or more helical elements, generally as illustrated in the prior embodiments. Other exemplary configurations are set forth in the embodiments described below.

Figure 3A:
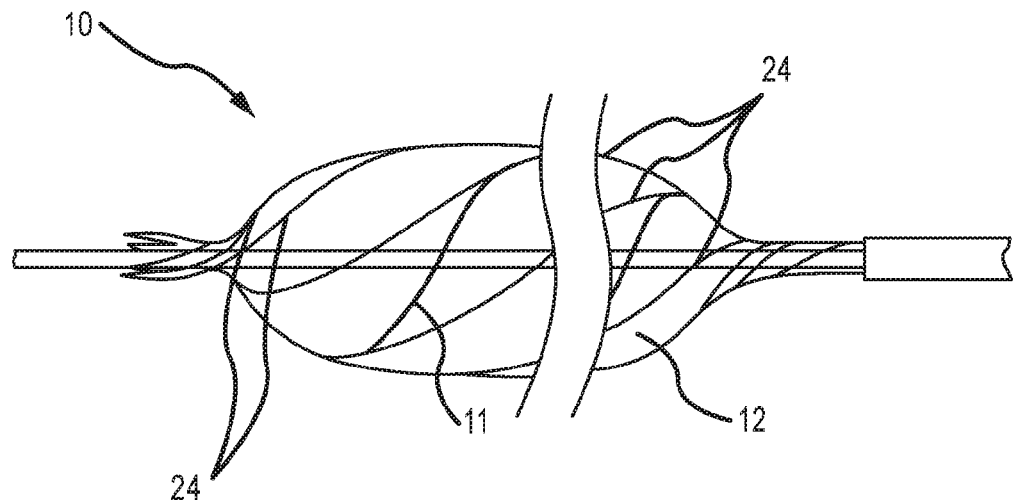
Figure 3B:
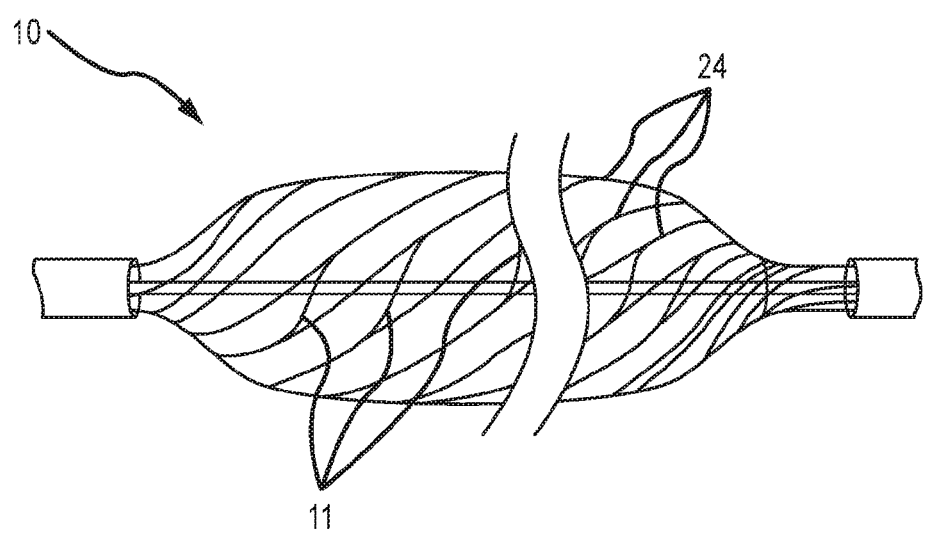

Reference is now made to FIG. 3 that shows a scoring structure in the form of a single wire 24 wrapped around a dilatation balloon 12 in a helical configuration. Additionally, with respect to the single wire 24 embodiment, stabilizing struts 11 may be disposed either randomly or evenly throughout the entire length of the helical unit 14 for added stability in the expansion and collapse of the helical scoring unit. As depicted by the spaces in FIGS. 3, 3A, and 3B, the helical assembly may be of any longitudinal length appropriate for the treatment site. The incorporation of stabilizing struts 11, however, may be most beneficial on either a relatively long helical assembly, e.g., any scoring structure longer than 50 mm, or a relatively short helical assembly that is designed to accommodate a balloon having a large diameter. For example, long scoring elements may be preferable when used to specifically address long, diffuse lesions of the femoro-popliteal arteries where a 100-300 mm scoring structure may be desirable—leading to fewer inflations and reduced procedure times. Conversely, short scoring elements on a 20-40 mm catheter may be preferable when used to treat a lesion within a large diameter vessel, requiring a balloon having a diameter of between 18-24 mm. With the addition of stabilizing struts to the helical assembly, the design and manufacture of lengthy and/or large diameter catheters becomes feasible.

Although the illustrated structure of an elastic metal, helical structure 10 may be preferred as it effectively maintains equal circumferential spacing of the scoring elements 24 as the shell 12 is inflated or otherwise expanded, other helical designs may be employed, such as those having a plurality of helical scoring elements, as illustrated in FIGS. 3A and 3B. In FIG. 3A, a cage 10 comprising six helical scoring elements 24, and a series of stabilizing struts 11, is disposed over an inflatable balloon 12. The construction of the catheter which carries balloon 12 and cage 10 will generally be the same as that described with respect to the foregoing description. FIG. 3B also describes an expansible cage 10 having a plurality of helical scoring elements 24, and a plurality of stabilizing struts 11, where the principal difference is that cage 10 includes twelve scoring elements in contrast to six scoring elements of FIG. 3A.

In other embodiments, the scoring structure of the present invention can have a non-helical configuration. Any design of scoring structure that can accommodate an increase in the diameter of the balloon 12 upon inflation, and return to its configuration when the balloon is deflated, is an appropriate design useful in the invention. At least a portion of the scoring elements will not be parallel to the longitudinal axis of the balloon catheter to enhance flexibility and improve scoring.

Referring now to FIGS. 4-6, alternative attachment elements are shown on an embodiment of an expandable scoring cage 140 comprising three helical scoring elements 142, supported by a plurality of stabilizing struts 11, which make up the intermediate scoring section. A first attachment element 146 comprises a single serpentine ring, as best illustrated in FIG. 5 while a second attachment element 148 comprises a pair of tandem serpentine rings 150 and 152, as best illustrated in FIG. 6. The use of such serpentine attachment structures is beneficial since it permits crimping of either or both of the structures onto the catheter body in order to fix either or both ends of the structure thereto. Usually, the single serpentine attachment structure 146 will be affixed to the catheter body while the double serpentine structure will be left free to allow movement of that end of the scoring cage to accommodate radial expansion of the underlying balloon.

Figure 7:
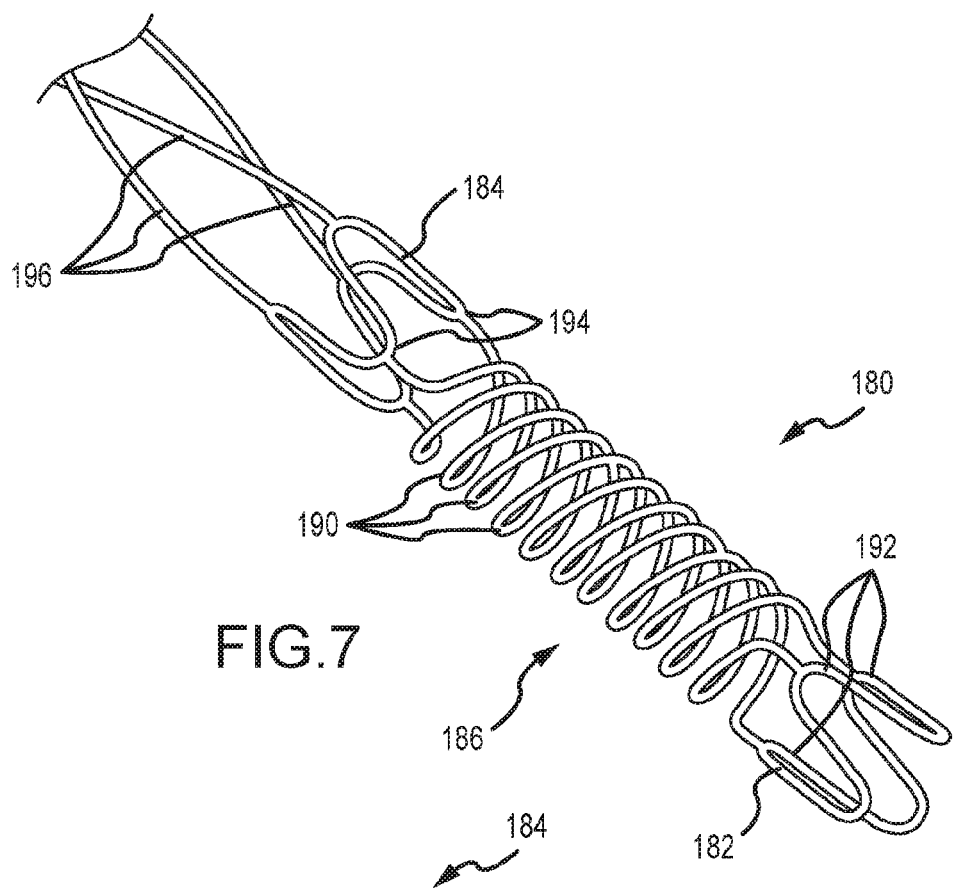
FIG. 7 illustrates an alternative mounting structure for a helical or other scoring structure.
Figure 8:
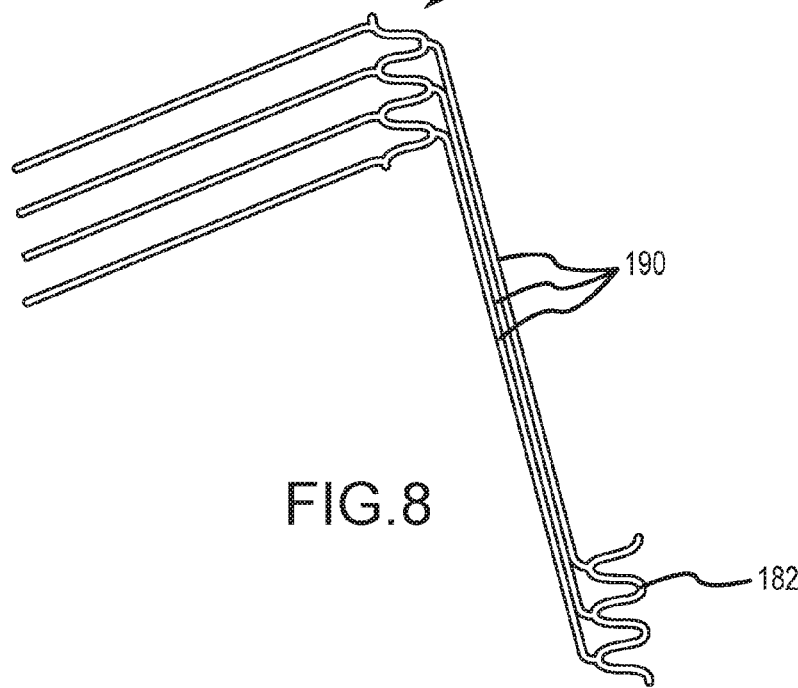
FIG. 8 illustrates the mounting structure of FIG. 7 shown in a rolled-out configuration.

Referring now to FIGS. 7 and 8, a further alternative embodiment of an attachment element useful in the scoring cages of the present invention is illustrated. Attachment element 180 includes a pair of serpentine rings 182 and 184, generally as shown in FIG. 7, in combination with a coil spring structure 186 located between said rings 182 and 184. The coil spring structure 186 includes but is not limited to three nested coil springs 190, each joining one of the bend structures 192 and 194 on the serpentine rings 182 and 184, respectively. The spring like structure can take on many forms that allow for linear and rotational movement during expansion and retraction of the scoring cage. The structure of the spring structure and adjacent serpentine rings can be understood with reference to the rolled-out configuration shown in FIG. 8.

The attachment structure 180 is advantageous since it permits a fixed attachment of the outermost ring 182 to the underlying catheter body while the inner ring 184 remains floating and expansion and contraction of the intermediate scoring section, comprising helical elements 196, is accommodated by the coil spring structure 186. Since the scoring cage is fixed to the catheter, any risk of loss or slippage from the balloon is reduced while sufficient compliance is provided to easily accommodate radial expansion of the intermediate scoring section. By attaching the structures 180 at at least one, and preferably both ends of the scoring cage, the risk of interference with a stent is reduced.

In some embodiments, collars, such as those shown in FIGS. 1 and 2, or attachment elements, such as those shown in FIGS. 4-6, may comprise a flexible material that allows the collar or attachment element to expand while being mounted over the balloon catheter and then be collapsed to the diameter of the catheter. The expandability of the collars and/or attachment elements may be achieved by a compliant memory material such as nitinol or a polymer, or by use of a flexible serpentine design as shown in FIGS. 4-6. Where collars are used, the collar may be shaped or have a slit down the circumference (not shown) so that the collar may be expanded during mounting over the balloon. Alternatively, the collar may be oversized to accommodate the balloon diameter mounting, and then crimped down to secure the secure the scoring structure to the catheter body.

The embodiments of FIGS. 7-8 comprise a spring-like element 186 to accommodate axial shortening of the scoring structure upon radial expansion. It will be appreciated that other metal and non-metal axially extensible structures could also be used in such attachment structures. For example, elastic polymeric tubes could be attached at one end to the scoring structures and at another end to the catheter body (or to a ring, collar or other structure which in turn is fixed to the catheter body).

The previous description of the disclosed embodiments is provided to enable any person skilled in the art to make or use the teachings herein. Various modifications to these embodiments will be readily apparent to those skilled in the art, and the generic principles defined herein may be applied to other embodiments without departing from the spirit or scope of the teachings disclosed herein. Thus, the scope of the disclosures herein is not intended to be limited to the embodiments shown and described, but is to be accorded the widest scope consistent with the general principles and novel features disclosed herein.

What is claimed is:

1. A catheter comprising:
   a catheter body;
   a balloon coupled to the catheter body;
   a helical scoring structure disposed over the balloon, the helical scoring structure comprising:
      a proximal end coupled to the catheter body;
      a distal end coupled to the catheter body;
      a plurality of helical elements that longitudinally extend from the proximal end to the distal end; and
      a plurality of S-shaped stabilizing struts, wherein each S-shaped stabilizing strut is disposed between and coupled to at least two adjacent helical elements,
      wherein the helical scoring structure is configured to radially expand in response to inflating the balloon, wherein at least one of the proximal end and the distal end moves axially as the helical scoring structure shortens to accommodate for radial expansion of the helical scoring structure during expansion of the balloon.

2. The catheter of claim 1, wherein the helical scoring structure is configured to rotate about a longitudinal axis of the plurality of helical elements as the balloon is expanded.

3. The catheter of claim 1, wherein the plurality of stabilizing struts are evenly spaced along the length of the helical scoring structure.

4. The catheter of claim 3, wherein the plurality of helical elements and the plurality of stabilizing struts are comprised of a metal.

5. The catheter of claim 4, wherein the plurality of helical elements and the plurality of stabilizing struts are comprised of Nitinol.

6. The catheter of claim 1, wherein the helical scoring structure is unattached to the balloon.

7. The catheter of claim 1, wherein the helical scoring structure has a length in a range of about 50 mm to about 300 mm.

8. The catheter of claim 7, wherein the balloon is capable of expanding to a diameter of about 2 mm to about 24 mm.

9. The catheter of claim 1, wherein each of the plurality of S-shaped stabilizing struts is coupled to the at least two adjacent helical elements at respective points on the at least two adjacent helical elements and the points are radially offset.

10. The catheter of claim 1, wherein the helical scoring structure comprises a longitudinal axis and each S-shaped stabilizing strut is generally parallel to the longitudinal axis.

11. The catheter of claim 1, wherein the S-shaped stabilizing struts extend generally longitudinally between the at least two adjacent helical elements.

* * * * *